United States Patent [19]
Zanakis

[11] Patent Number: 5,830,158
[45] Date of Patent: Nov. 3, 1998

[54] DYNAMIC SYSTEM FOR DETERMINING HUMAN PHYSICAL INSTABILITY

[76] Inventor: Michael Zanakis, 1 Ken Pl., Port Jefferson Station, N.Y. 11776

[21] Appl. No.: 761,653

[22] Filed: Dec. 6, 1996

Related U.S. Application Data

[63] Continuation-in-part of Ser. No. 685,951, Jul. 22, 1996, Pat. No. 5,627,327.

[51] Int. Cl.$^6$ .................................................. A61B 5/103
[52] U.S. Cl. ............................................................ 600/595
[58] Field of Search ................................... 600/587, 595; 73/862.042

[56] References Cited

U.S. PATENT DOCUMENTS

| | | | |
|---|---|---|---|
| 4,463,946 | 8/1984 | Wallace et al. | 272/111 |
| 4,548,289 | 10/1985 | Mechling | 600/587 |
| 4,885,687 | 12/1989 | Carey | 600/587 |
| 5,080,109 | 1/1992 | Arme, Jr. | 600/595 |
| 5,303,715 | 4/1994 | Nashner et al. | 128/782 |
| 5,419,521 | 5/1995 | Matthews | 298/278 |
| 5,435,320 | 7/1995 | Seitz | 600/595 |
| 5,551,445 | 9/1996 | Nashner | 600/587 |

*Primary Examiner*—Max Hindenburg
*Assistant Examiner*—Pamela L. Wingood
*Attorney, Agent, or Firm*—Michael Ebert

[57] ABSTRACT

A dynamic system adapted to test a patient to determine the degree to which his physical stability is impaired and therefore predisposes the patient to injurious falls. The system includes an unsteady platform supported at a raised position above ground and free to rock about a horizontal X-axis and about a Y-axis which intersects the X axis at the center of the platform and is normal thereto so that the orientation of the platform is changeable relative to these axes. Mounted on the platform are electronic clinometers that yield signals which are a function of the deviation of the platform from the horizontal X and Y axes and therefore depend on the changing orientation of the platform when a patient to be tested stands thereon. These signals are fed to a computer whose output is applied to a video monitor having a display screen on which is presented a cursor the position of which is controlled by the signals. The standing patient, while viewing the screen, is required to so shift his weight on the platform as to alter its orientation to produce signals causing the cursor to travel from the center of the screen toward a computer-generated target presented on one corner of the screen, and to then acquire the target. The computer measures and scores the time it takes for the patient to cause the cursor to acquire the target as well as other variables that reflect the relative instability of the patient. These scores, taken together, define a stability index useful in deciding how then to treat the patient to improve his condition.

14 Claims, 3 Drawing Sheets

DYNAMIC SYSTEM FOR DETERMINING HUMAN PHYSICAL INSTABILITY

RELATED APPLICATION

This application is a continuation-in-part of the Zanakis application Ser. No. 08/685,951, filed Jul. 22, 1996 now U.S. Pat. No. 5,627,327, having the same title, the entire disclosure of which is incorporated herein by reference.

BACKGROUND OF INVENTION

1. Field of Invention

This invention relates generally to apparatus adapted to determine the degree to which the physical stability of a patient is impaired, and more particularly to a dynamic system including a computer for this purpose which is responsive to shifts in the weight of a patient standing on an unsteady platform to provide measurements from which are derived a stability index useful in deciding how then to treat the patient so as to improve his condition.

2. Status of Prior Art

The concern of this invention is with the physical balance or stability of a human subject and the degree to which balance is impaired and therefore requires corrective treatment appropriate to the subject's condition. Whether considered in mechanical terms or in the context of human physical behavior, stability is that property of a body which causes it to develop forces opposing any position or motion-disturbing influence. Stability therefore depends on being able to reach a state of equilibrium or balance.

An individual whose physical stability is impaired is then predisposed to falling down. The human body incorporates a complex balance-control mechanism, and any imbalance therein, regardless of its origin, leads to falling and this may have serious consequences.

The present invention resides in a dynamic system adapted to determine by means of an unsteady platform on which the subject being tested stands and a computer associated with the platform, the degree to which the stability of the subject is disturbed. The stability index yielded by the system makes it possible to then decide on the nature of the treatment appropriate to the subject's condition. (In the specification, the terms "subject" and "patient" are used interchangeably.)

The Kellogg International Work Group defines a fall as "an event which results in a person coming to rest inadvertently on the ground or other lower level, other than as a consequence of the following: sustaining a violent blow; loss of consciousness; sudden onset of paralysis, as in a stroke; or an epileptic seizure." A fall resulting from impaired stability lies within this definition, for the individual falls only because he is unable to maintain his balance.

As revealed by the available statistics, fatal falls in the United States often occur in elderly individuals, the mortality rate due to falls rising markedly with advancing age. Each year, a significant percentage of those individuals over 75 years of age who are brought to hospital emergency rooms are there because of a fall-related injury. And about 70% of general injury treatment in hospital emergency rooms in this age group is imputed to falling accidents.

Many senior individuals exhibit a proclivity for falling due to any number of neuromusculoskeletal dysfunctions. Brittle bones combined with slower reflexes result in bone breakage and other associated injuries and these are enormously expensive to repair. Several factors including age or sex are involved in identifying high-risk individuals, the probability of falling increasing exponentially with advancing age. Women appear to be at higher risk in most age groups.

Another risk factor is osteoporosis which decreases bone resistance to mechanical injury, thereby increasing the risk of compression fractures. This then predisposes certain bones (hip, pelvis, forearm, vertebrae) to possible fracture. It is generally recognized that chronic diseases causing cardiovascular and neuromuscular dysfunction can significantly increase the risk of falling. Other factors also contribute to falls, such as gait and balance disturbances, poor vision, a disturbed mental state, and the use of medication or alcohol.

To prevent falls or to reduce their possibility, it is known to use screening techniques to identify high-risk individuals. Once a high-risk individual is identified, steps can then be taken to remove or minimize risk factors, such as by strengthening weak muscles or altering a drug regimen to avoid side effects resulting in a loss of balance. But an effective and reliable technique to screen such high-risk individuals has not heretofore been realized.

Thus numerous bio-mechanical techniques have been developed to analyze balance, but these have largely been static tests lacking components of dynamic response, or they were aimed at neuromuscular analysis and therefore not practical for screening. These and other previously known tests fail to take into account the matter of function; i.e., the physical abilities a subject actually needs in order to carry out daily activity. A static test, such as posturography, determines the amount of sway a subject exhibits when the subject is standing with his eyes open or closed. Such posturography tests have also evolved into a pseudo-functional test in which a subject stands on a static (non-moving) platform and shifts his weight in performing certain motor tasks while a computer monitors the results. Such motor tasks are similar to tracking a target, or using body sway to cause a video cursor to travel around a video "racetrack."

A known modification of pseudo-functional static testing is the incorporation therein of a bio-mechanical test using a force platform which pivots under the ankle and can slide front-to-back. This arrangement enables the researcher to induce sway and thereby determine the degree to which the subject can compensate by changing his posture.

These known testing techniques all suffer from a major flaw, for they are not really functional assessments. Since instability resulting in falls occurs during imbalance while walking (not standing still), in order to be effective a functional test must determine the ability of the subject to maintain balance during the performance of a task requiring body motion. Moreover, static or pseudo-functional balance testing is only effective for initial screening, in that patients gradually adopt a posture for control strategy after becoming familiar with the test conditions. Quantitative measures of adaptive abilities are therefore needed to make testing of equilibrium more useful clinically.

In equilibrium control, two information processes enable the subject to stand and walk over a variety of surfaces and conditions. There is redundant information supplied by sensory modalities related to orientation, these being somatosensory, vestibular and visual, all three having different frames of reference. There is also weighted information whereby the system modifies the relative importance of these inputs. However, under abnormal physiological conditions, such as when the subject suffers from a disease, either the inputs are disturbed or the weighted information may not be suitable for effective control of equilibrium.

As a consequence, compensation for the balance deficit may require another adaptive strategy. Indeed, it is the ability of a subject to modify balance strategy for proper equilibrium in response to various environmental challenges that makes quantitative assessments difficult. It is therefore necessary to utilize a system for equilibrium testing that incorporates a variety of support surface conditions that influence the vestibular system and the somatosensory input, yet simultaneously relies on a variety of visual conditions, all successively imposed on the subject being tested. A dynamic system in accordance with the invention does just that, and enables quantification of the subject's responses under such varied conditions.

Of prior art interest is the stability test disclosed in the article by Lord et al. "Exercise Effect on Dynamic Stability in Older Women" published in Arch. Phys, Med. Rehabit. Vol. 77 March 1996 in which a subject being tested is coupled to a recording pen movable on an undulating track.

Also of prior art interest as showing platforms supported by elastic members on which a patient stands during testing, which elastic members generate a reactive restoring force to the supported platform which is proportional to the magnitude of deflections from equilibrium are the following patents:

Heurte 5,360,015 (November 94)
Wallace et al. 4,463,946 (August 84)
McFarland 3,826,145 (July 74)
Roost 5,186,062 (February 93)

In the above-identified Zanakis co-pending application, there is disclosed a dynamic system adapted to test a patient to determine the degree to which his physical stability is impaired. The system includes a stable platform yielding signals that depend on the magnitude and direction of the force applied to the platform face. The platform is rendered unsteady by a convex rocker dish resting on the face of the platform and having a flat top on which the patient stands. The resultant signals which are a function of the orientation of the flat top of the dish relative to the platform face are fed to a computer whose output is applied to a video monitor having a display screen on which is presented a cursor which position is controlled by the signals.

The standing patient, while viewing the screen, is required to so shift his weight on the rocker dish as to alter the orientation of the flat top to produce signals causing the cursor to travel from the center of the screen toward a computer-generated target presented on one corner of the screen and to then acquire the target. The computer measures and scores the time it takes for the patient to cause the cursor to acquire the target as well as other variables that reflect the relative stability of the patient. These scores, taken together, define a stability index useful in deciding how then to treat the patient to improve his condition.

In the dynamic system disclosed in the above-identified Zanakis copending patent application, mounted below the stable platform is a transducer responsive to the force applied to the face of this platform by a convex rocker dish resting on this face. When the patient to be tested stands on the flat top of the convex dish, the signals then generated by the transducer are a function of the direction and magnitude of the applied force along three mutually-perpendicular axes of movement (X-Y-Z). Hence these signals depend not only on how the standing patient shifts his weight on the dish to alter the orientation of the flat top of the dish relative to the horizontal plane, but the signals are also a function of the patient's body weight. Hence a heavy patient produces transducer signals of greater magnitude than a lighter patient.

SUMMARY OF INVENTION

In view of the foregoing, the main object of this invention is to provide a dynamic system making use of an unsteady platform associated with a computer to determine the degree to which the physical stability of a patient standing on the platform is impaired, the system being independent of the weight of the patient.

A significant feature of a system in accordance with the invention is that the patient performs a task on an unsteady platform, and as the platform shifts the patient's adaptive abilities must change rapidly to accommodate the shifting platform and the performance of the task.

Also an object of this invention is to provide a system of the above type in which a computer analyzing the performance of a patient standing on an unsteady platform produces an accurate reading of the patient's performance regardless of the physiological or psychological conditions responsible for the patient's impaired stability.

A salient advantage of a dynamic system in accordance with the invention is that it is capable of determining the balance and equilibrium functions of the subject being tested. A comprehensive functional test is performed by taking into account the various changes in posture required to maintain equilibrium under various visual, sensory or vestibular stimuli. This functional equilibrium and balance test makes it possible to predict the likelihood of a serious fall in elderly individuals or other patients.

Though there are many motion analysis facilities throughout the United States, these are mainly focused on a single diagnosis related to a specific disease such as Parkinson's disease or cerebral palsy. A system in accordance with the invention provides an integrated assessment using a bio-mechanical device and computer software that yield rapid and reproducible results.

A computer-assisted motion analysis system in accordance with the invention reliably measures bio-mechanical functions under controlled physical conditions, the system assessing components of movement, such as motor reaction time, movement time, velocity and postural stability. The test uses a computer-generated video task performance program requiring the patient to track a video target with a cursor projected onto a video screen. The cursor is guided in real time by the patient moving his body on an unsteady platform which senses changes in the patient's center of gravity.

The results derived from the patient's motion in the course of specific tests are calculated and scores are obtained, which assigns the patient to a low, medium or high instability category. The resultant stability profile can be used to predict the likelihood of a fall. Ultimately, the scores serve as a guide to appropriate preventive measures, such as physical therapy (muscle strengthening), exercise, environmental changes (e.g., installing home handrails), orthotics and drug therapy. These preventive measures greatly reduce the probability that a severe fall will occur.

Briefly stated, these objects are accomplished by a dynamic system adapted to test a patient to determine the degree to which his physical stability is impaired, and therefore predisposes the patient to injurious falls.

The system includes an unsteady platform supported at a raised position above ground and free to rock about a horizontal X-axis and about a Y-axis which intersects the X axis at the center of the platform and is normal thereto so that the orientation of the platform is changeable relative to these axes. Mounted on the platform are electronic clinometers that yield signals which are a function of the deviation of the platform from the horizontal X and Y axes and therefore depend on the changing orientation of the platform when a patient to be tested stands thereon.

These signals are fed to a computer whose output is applied to a video monitor having a display screen on which is presented a cursor the position of which is controlled by the signals. The standing patient, while viewing the screen, is required to so shift his weight on the platform as to alter its orientation to produce signals causing the cursor to travel from the center of the screen toward a computer-generated target presented on one corner of the screen, and to then acquire the target. The computer measures and scores the time it takes for the patient to cause the cursor to acquire the target as well as other variables that reflect the relative instability of the patient. These scores, taken together, define a stability index useful in deciding how then to treat the patient to improve his condition.

BRIEF DESCRIPTION OF DRAWINGS

For a better understanding of the invention, as well as other objects and features thereof, reference is made to the accompanying drawings wherein.

DETAILED DESCRIPTION OF INVENTION

The Dynamic System (First Embodiment)

Figures 1, 2, 3:
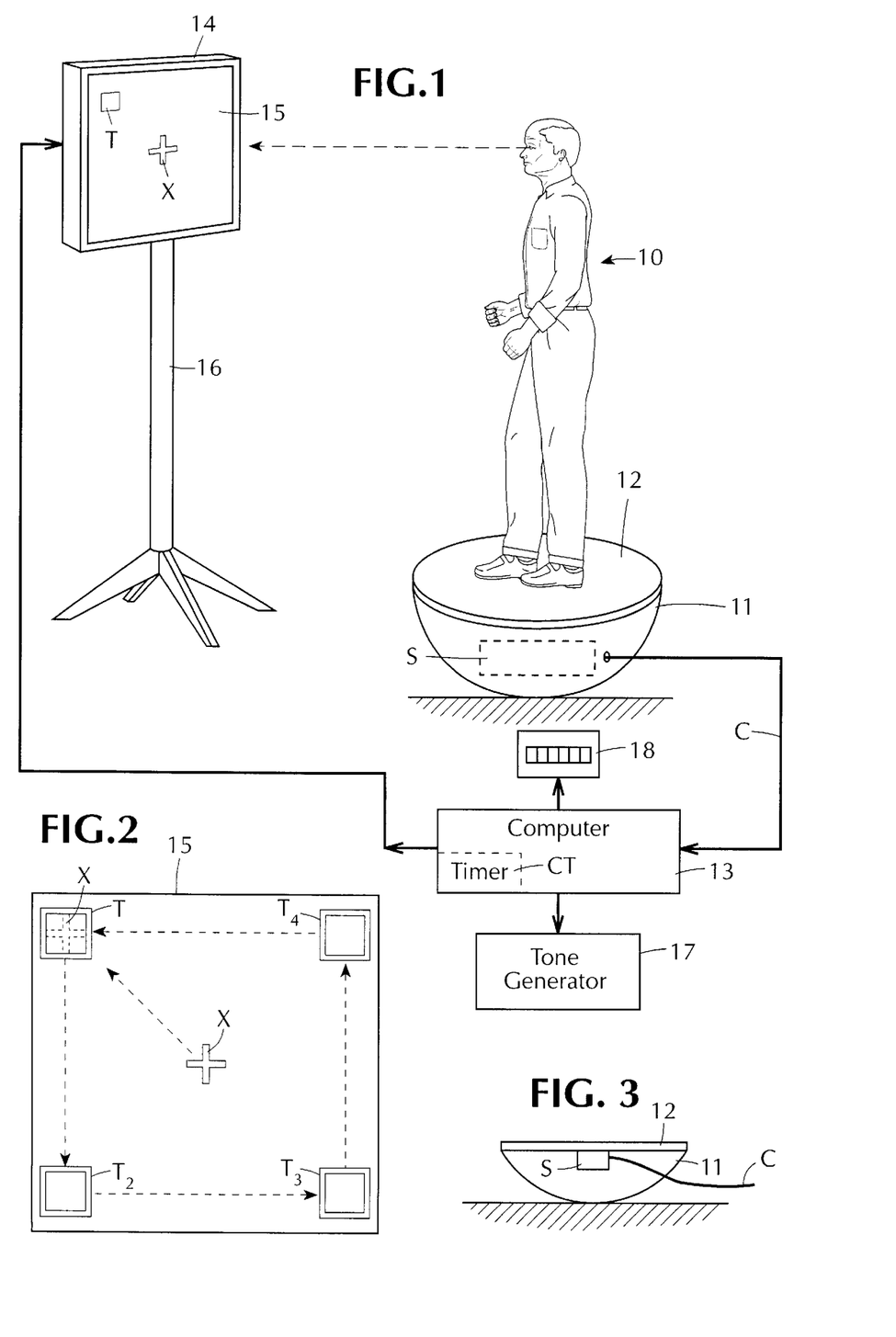
FIG. 1 schematically illustrates a dynamic system in accordance with the invention in which a patient to be tested stands on an unsteady platform in the form of a convex dish.
FIG. 2 shows the screen of the video monitor included in the system.
FIG. 3 is a separate view of the convex dish which forms the unsteady platform of the system and the inclination sensor box on the underside of the flat top of the dish.

Referring now to FIG. 1 of the drawing, shown in this figure is a dynamic system in accordance with one preferred embodiment of the invention which functions to determine the degree to which a human subject (patient 10) suffers from an impaired physical stability and is therefore predisposed to injurious falls. The cause or source of such instability is not the concern of the system, but only the degree to which it exists. Obviously a patient whose physical stability is only slightly impaired has a much lower predisposition to falling down than one having a much greater degree of impairment. An accurate determination of the degree of impairment is therefore a useful guide to a physician or therapist prescribing a proper treatment to improve the patient's condition.

The system includes an unstable platform in the form of a shallow convex rocker dish 11 of large diameter provided with a flat face 12 on which the patient stands when the dish is placed on the floor of a test facility. In an actual embodiment dish 11 is formed of steel and is therefore heavy, and has a 30 inch diameter and an 8 foot radius of curvature.

Hence the rockability of the dish is limited and patient 10 standing on its flat top face 12 remains at an erect position as he rocks the dish in a manner to be later explained.

Mounted on the undersurface of the flat top face 12 of dish 11 is a box S containing inclination sensors which yield signals that reflect the changing orientation or tilt of the flat face with respect to the horizontal plane which it normally occupies. When dish 11 rests on a horizontal ground surface or floor, and no patient stands thereon, the flat face then lies in a horizontal plane.

Figures 4, 5, 6, 7, 8:
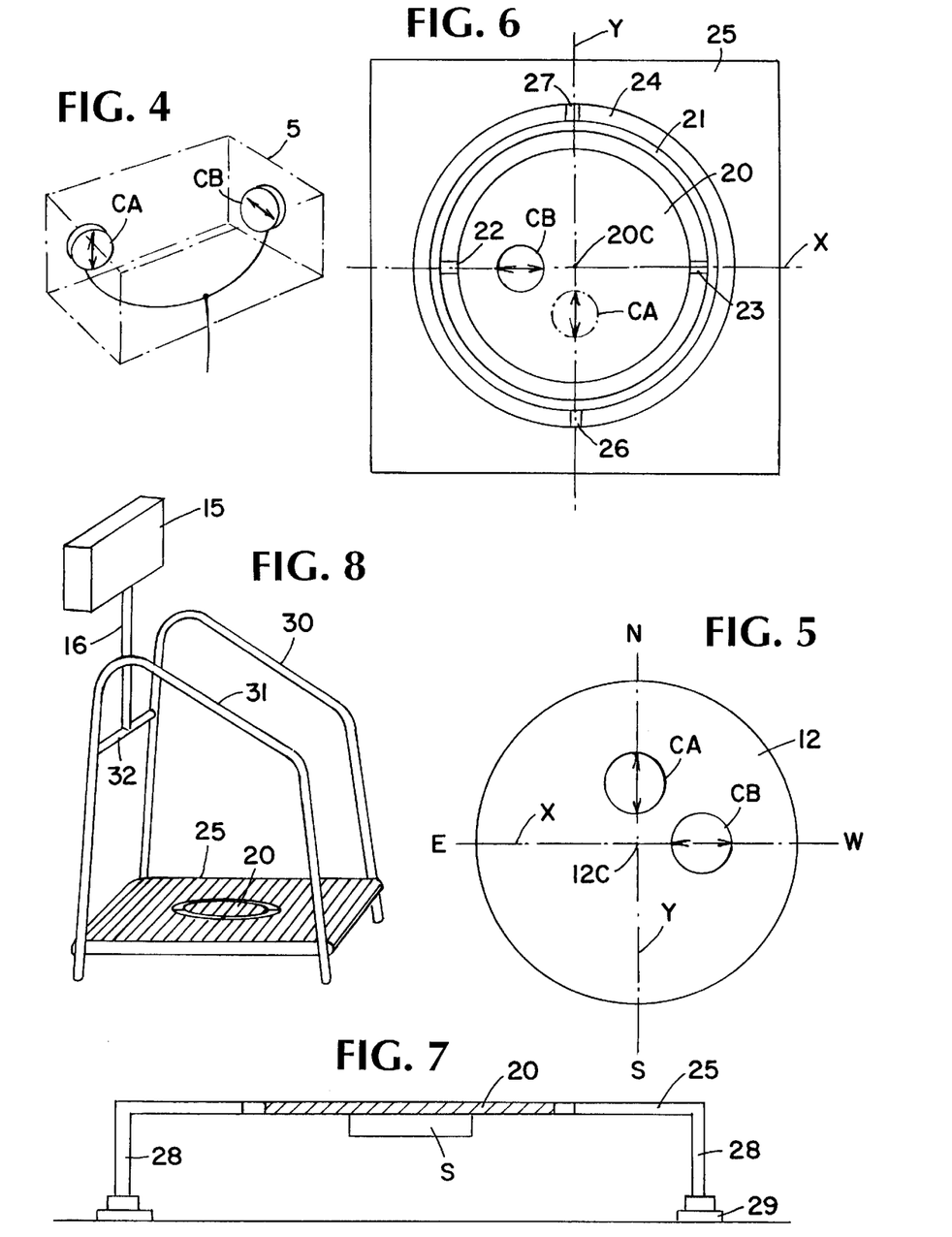
FIG. 4 is a separate view of the inclination sensor box.
FIG. 5 shows the geometric relationship of the two clinometers in the sensor box to the flat top of the dish.
FIG. 6 is a plan view of a second embodiment of an unsteady platform constituted by a disc hingedly supported within a gimbal that lies within an opening in a base and hinged thereto.
FIG. 7 is a side view of the unsteady platform shown in FIG. 6.
FIG. 8 is a perspective view of the unsteady platform shown in FIGS. 6 and 7 in which the platform is flanked by rails which can be held by a patient standing on the platform.

As shown in FIGS. 4 and 5, the box of sensors S contain a pair of electronic clinometers CA and CB. An instrument of this type which acts as an electronic level, when placed on a movable body, is adapted to produce an analog signal whose magnitude and polarity depend on the direction and the extent to which the body deviates from a horizontal plane.

It will be seen in FIG. 5 that the circular flat face 12 at the top of convex dish 11 lies in a horizontal plane having a horizontal X axis that runs through center 12C of the dish in the East-West direction, and a horizontal Y axis that intersects the X axis at the center 12C and is at right angles thereto, the Y axis running in the North-South direction.

Clinometer CA is placed under top face 12 of the convex dish acting as an unstable platform in line with its horizontal Y axis, while clinometer CB is placed under the top face in line with its X axis. Hence when top face 12 lies in the horizontal plane containing the horizontal X and Y axes, the analog signals then yielded by clinometers CA and CB are both at a null value.

But when a patient being tested stands on the flat face 12 of the convex dish and shifts his weight thereon to more or less tilt the face at any angle within a 360 degree compass, the resultant signals from clinometers CA and CB reflect the compass direction and degree of the tilt.

If therefore top face 12 is tilted down by the patient standing thereon in the North direction with respect to the horizontal Y axis, clinometer CA which lies on this axis will then produce a signal whose polarity indicates this down tilt and whose magnitude then indicates the extent of this tilt. But clinometer CB aligned with the XY axis will then yield a null signal, for the tilt is neither in the East or West direction.

But when the tilt is in a direction intermediate Cardinal point compass directions, such as North-West or South-East, then signals will be yielded by clinometers CA and CB which reflect these intermediate compass directions and therefore the direction and extent to which flat face 12 of the dish is tilted by a patient standing thereon.

The signals yielded by clinometers CA and CB are fed via a cable C to the data acquisition board of a digital computer 13 which process the data, the output of which is applied to a video monitor 14 having a large, generally rectangular video display screen 15. A preferred computer for this purpose is a IBM386 or a similar unit that includes a high-speed data acquisition board for an analog-to-digital input. The IBM unit is capable of handling 6 channels of input at approximate 100 MHz.

Generated in computer 13 and presented on screen 15 of video monitor 14 is a cursor X having a cruciform or cross-like formation, very much like the familiar Red Cross symbol. As best seen in FIG. 2, cursor X which is formed by a vertical bar intersected at its midpoint by a horizontal bar of the same length, is initially at the center of video screen 15. In an actual embodiment, the dimensions of the cursor X are such that the cross fits within a three-inch imaginary square and has a bar thickness of ⅛ inch. Hence cursor X is clearly visible to patient 10 standing six feet away from the screen.

Also presented on screen 15 is a computer-generated target T formed by a square box whose dimensions correspond to that of the imaginary square into which cursor X fits, the square box of target being framed by a square border. Thus target T has a 3 inch square box and a border whose four sides have a ⅛ inch thickness. When the center point of the cross of cursor X lies within the box of target T, it is then said to have acquired the target. But if the center point of the cursor cross lies in the border of the target or is outside the border, the cursor does not then acquire the target.

Target T is initially presented on video screen 15 adjacent to its upper left corner, as best seen in FIG. 2. Target T is made distinguishable from cursor X by giving it a different color, hue or brightness. The test to which patient 10 is subjected, requires him to move the signal-controlled cursor X toward target T so that it acquires the target. In order to move the cursor, the patient must so rock the unsteady dish on which he is standing as to produce unstable platform signals causing the cursor to move in the desired direction.

The patient standing on the flat face of the dish must exert neuromuscular control of his posture to maintain his balance while undergoing a test.

Test Procedure

When patient 10 to be tested stands still with his feet on the central region of flat top face 12 of convex dish 11, the flat top face is then oriented so as to lie in the horizontal plane. In this initial state, the null signals then yielded by clinometers CA and CB cause cursor X responsive to these signals to occupy the center position of video screen 15, as shown in FIG. 2.

In the course of a test, patient 10 standing on rocker dish 11 which acts as an unstable platform and observing cursor X on video screen 15 is required to shift his weight on the dish and therefore his center of gravity to tilt the dish so that the resultant signals yielded by clinometers CA and CB cause cursor X to travel from its initial center position on the screen in a direction and to an extent determined by the manner in which the patient shifts his weight and in doing so modulates these signals.

By shifting his weight forward and to the left, flat top 12 of the dish is then tilted in the North-East direction to produce signals causing cursor X to travel from the center of the screen toward target T and to acquire the target which in the first phase of the test procedure is located adjacent to the upper left corner, or North-East position of video screen 15.

Computer 13 is provided with a tone generator 17 which produces an audible tone which acts as a cue for the patient hearing this tone. As long as cursor X is visibly within target T, the audible tone has a high-frequency, such as 800 Hz. Should cursor X move out of the target, so that the center of the cursor cross is outside of the square box of the target, the audible tone remains "on" but then has a lower frequency, such as 500 Hz. Hence the frequency of the tone tells the patient whether or not target T has been acquired by cursor X.

Included in computer 13 is an internal timer CT, the computer being programmed to cause the timer to start a count of 5 seconds when cursor X moves away from its center position on the screen as a result of a rocking motion imparted to dish 11 by patient 10 standing on its flat top 12 and acquires the target. During this 5 seconds timed interval, the patient must try, as best as he can, to keep cursor X within target T.

At the conclusion of the 5 seconds timed interval in the first phase of the test procedure during which target T is positioned adjacent the upper left corner of video screen 15, computer 13 then instantly shifts the target to a position adjacent the bottom left corner of the screen, as indicated by target $T_2$. During this change in target position, the position of cursor X remains unchanged.

When patient 10 is presented with target $T_2$ at the bottom left corner of video screen 15, this begins the second phase of the test procedure in which patient 10 must now seek to have cursor X acquire target $T_2$. To do so, patient 10 must now shift his weight on rocker dish 16 to te rear and left to tilt the flat face 12 in the North-West direction in order to produce platform signals causing cursor X to move target and acquire target $T_2$. And the patient must do so during the timed 5 seconds interval in the second phase of the test procedure.

At the conclusion of this 5 seconds interval, computer 13 then brings about another shift of the target position to present a target $T_3$ at the bottom right corner of screen 15 as shown in FIG. 2, this being the third phase of the test procedure.

Now the patient must shift his weight on the rocker dish to repeat the process to cause cursor X to move toward and acquire target $T_3$. At the conclusion of the third phase, the computer moves the target to the upper right corner of the screen to present a target $T_4$. The patient must again shift his weight to repeat the process in the fourth phase of the test procedure. Finally, the target again shifts to the top left corner of the screen, and this too must be acquired.

The patient actually is given as much time as he wants to go from target to target. However, once a target is acquired, the 5 second timer CT proceeds to time and the patient has only five seconds to keep the cursor stable; that is within the box of the target.

Five seconds is allowed once a target is acquired whether or not the patient in any one phase of the test procedure is unable to keep cursor X within the confines of the target then being presented on the screen regardless of how many times during this period the border of the target is traversed by the cursor. Computer 13 "times out" after 60 seconds if a target cannot be acquired at all and acts to shift the target to the next corner of the screen.

Measurements

Computer 13 is programmed by appropriate software to carry out measurements of the following values, each one of which represents a variable that depends on the relative stability of the patient tested.

Value A "Reaction Time" (RT)

Variable RT represents time in seconds it takes for a patient, when first presented with a target at one corner of the screen, to then cause the cursor X to begin moving toward the target. In a physiological sense, this variable represents the time elapsed between cognition and the initiation of motor activity.

Value B "Movement Time" (MT)

Variable MT represents the time it takes in seconds for the patient to cause cursor X to move toward and be acquired by the target. This variable therefore represents the time of acquisition from target to target.

Value C "Average Velocity" (V)

Variable V which is expressed in inches per second, is calculated as the total distance travelled by the cursor once acquired by the target, divided by five seconds. This variable reflects oscillation of the cursor with respect to the target as a result of unsteadiness on the part of the patient. Hence it provides an indication of the patient's ability to maintain steadiness.

Value D "Stability" (S)

Variable S represents the cumulative time in seconds within the target zone divided by the total number of times the cursor moves beyond the border of the target. This variable is therefore indicative of the patient's ability to provide sufficient neuromuscular control to maintain the cursor within the target.

The objective of the test procedure is to determine the degree of stability patient 10 is capable of attaining under normal conditions, not under conditions in which the patient is functioning poorly. Hence the patient is urged by the operator of the system to acquire the target as rapidly as it is possible for him to do so, and the patient is encouraged in the course of the test procedure to do the best he can in order to get the highest possible score. The best score the patient can attain affords the most accurate reading of the actual degree to which the patiert's stability is impaired.

To this end, the five-phase test procedure is carried out three times, the first two being trial runs whose scores are examined and then discarded. The values achieved in the third and final run are the only ones used and averaged for these are the most reliable indications of the patient's degree of instability.

The scores produced by the third run taken together, afford a qualitative dynamic profile of the physical characteristics associated with volitional movement of the patient during a "functional" test. This profile represents a stability index and is predictive of the probability of a fall.

A slow reaction time RT is indicative of a patient having poor neuromuscular control. A patient having a slow reaction time cannot reflexively adapt to the changing environment with adequate postural adjustments. A slow movement time MT generally indicates a bradykinesia, or slowness of movement. This is often found in parkinsonism, and is also a major factor in inadequate postural control.

A velocity (V) score of 5 indicates cross of the cursor over and into the target box only, with no subsequent movement over the target's border to the outside of the box. A velocity (V) score of 1 indicates that the subject moved the cursor over the target borders 5 times (regardless of the direction of movement). It therefore indicates that the subject is less stable than a subject who scores a 5. The higher this score, the more stable the balance and compensatory mechanism.

A velocity (V) of approximately 3 inches per second (ips) and a stability S of approximately 5 indicates that the subject rapidly and effectively acquires the target and remained in the target zone. A higher velocity is usually associated with unsteadiness, and therefore a lower stability score, since the subject tends to oscillate the cursor rapidly about the target zone. Conversely, a slower velocity V and either stability S means that while the subject can maintain steadiness within the target zone, the postural responses needed are slow and not as effective. Slow velocity V and poor stability S indicates compounded difficulties in neuromuscular control. The scores of values A, B, C and D yielded by computer 13 are printed out on a printer 18 associated with the computer, the printout providing a stability index indicative of the degree to which the patient's stability is impaired.

Usefulness of Results

The system in accordance with the invention acts to measure quantitatively specific components of movement, the computer assessing various movement parameters associated with balance. In practice, the stability index data derived from one patient can be compared to those derived from other patients in a data base, including normal young individuals who were subjected to the same test procedures. By means of software, one can correlate the test results and assign stability scores to each patient to determine his degree of instability and the concomitant probability of falling.

All patients should first be screened to grossly determine their motor performance using subjective assessments, as well as a history and a physical. For example, determining that a the patient requires mechanical support (cane, walker, etc.) would place the patient in a high risk fall category. However, in patients without overt signs of instability, the system will provide an objective and quantifiable assessment of their instability, (i.e., a fall index).

A physician can use this index as the rationale for prescribing specific treatments. Such treatments can range from referral to specialists (for example, in orthopedic surgery) to consultation or referral to a physical therapist, who can then prescribe, for example, orthotics or exercise. In this way the physician can more reliably insure that the patient will be able to avoid a debilitating fall.

Since the system acts to assess stability, other uses of stability analysis aside from fall prediction are then possible. Motor dysfunctions associated with disease states such as Parkinson's disease can be quantified to determine the effectiveness of a drug regimen on that disease, or even the progression of the disease (i.e., its progressive motor deterioration).

Also, various states of muscle weakness can be quantified, for prescribing and targeting proper muscle strengthening therapies. This is important from the perspective of rehabilitation of injured limbs and postoperative procedures whereby recovery can be monitored to efficiently correlate length of hospital stay or the amount of rehabilitation required. Care of the elderly with regard to stability testing for fall prediction and management can also be extended to treatment of musculoskeletal dysfunction, and care as well as for muscle strengthening to alleviate a weakness. Finally, from a sports medicine perspective, the system is useful, for it can provide information regarding motion and balance during certain physical activities whereby the activity can be modified to alter performance.

Dynamic System (Second Embodiment)

In the dynamic system shown in FIG. 1, the unstable platform takes the form of a convex dish resting on the floor of a test facility. In order for the flat face of this dish to normally lie in a horizontal plane so that it is tilted only when a patient being tested stands on this face and shifts his weight thereon, it is essential that the surface on which the convex dish rests be horizontal and also perfectly flat. It is also necessary that the dish which is made of steel be exactly balanced so that at rest the flat face lies in the horizontal plane. These conditions are not easily satisfied.

In the unstable platform shown in FIGS. 6 and 7, the platform takes the form of a circular disc 20 made of steel or other high-strength material having a diameter of 20 feet or greater so that a patient to be tested can conveniently stand thereon.

Disc 20 is placed within a circular gimbal 21 formed by a metal ring whose inner diameter is greater than that of the disc. Disc 20 is hinged to gimbal 21 by a pair of diametrically opposed bearing 22 and 23 which are in alignment with a horizontal X axis extending through center 20C of the disc.

Gimbal 21 lies within a circular opening 24 formed in a rectangular base plate 25, the diameter of opening 24 being greater than the outer diameter of gimbal 21. Gimbal 21 is hinged to base plate 25 by a pair of diametrically-opposed bearings 26 and 27 which are in line with a horizontal Y axis extending through the center of disc 21 at right angles to the X axis. Hence disc 20, gimbal 21 and plate 25 are concentric with each other.

As shown in FIG. 7, base plate 25 supporting the unstable platform disc 20 is held at a raised position above ground by four corner legs 28, each having a screw-in foot 29. By turning this foot one can adjust the height of the leg to which it is coupled to the extent necessary to maintain the raised base plate 25 at a stable position in a horizontal plane. Thus if the face plate is placed on an uneven floor, one can by adjusting the legs and with a spirit level checking the surface of the base plate, properly place the base plate in a horizontal plane.

Mounted on the underside of disc 20 are the electronic clinometers CA and CB in sensor box S, clinometer CA being placed in line with the horizontal Y axis (North-South) and clinometer CB being placed in line with the horizontal X axis (East -West). Hence the clinometer arrangement is the same as that shown in FIG. 5 in connection with the flat face of the convex dish.

The manner in which the clinometers are coupled to computer 13 as shown in FIG. 1 and in which the dynamic system operates to test a human subject is the same as previously described in connection with the first embodiment of this system.

An advantage of the gimbal arrangement shown in FIGS. 6 and 7 over a convex dish as an unsteady platform as shown in FIG. 1, is that if the patient being tested while standing with both feet on disc 20 within the gimbal is highly unstable and fears he is going to fall, he can steady himself by putting one foot on the stable base plate 25 surrounding the disc.

Because many patients undergoing a stability test may be elderly or in a somewhat disabled condition, to make it easier for a patient to mount base plate 25 and put his feet on the unsteady disc 20, in the arrangement shown in FIG. 8, base plate 25 is provided on either side with upstanding parallel rails 30 and 31. These rails are so shaped as to assist a patient holding on to these rails to mount the stable base plate 25 at its right end and to move with his feet onto the unsteady disc 20.

Instead of placing video monitor 15 away from the unsteady platform of which the patient being tested stands, as in FIG. 1, in the arrangement shown in FIG. 8 video monitor 15 is supported by adjustable stand 16 which is anchored on a cross bar 32 bridging rails 30 and 31 at the left side of the base plate.

Hence the patient standing on disc 20 can look directly at the video monitor whose height is adjusted to be in line with the patient's eyes.

Dynamic System (Third Embodiment)

Figure 9:
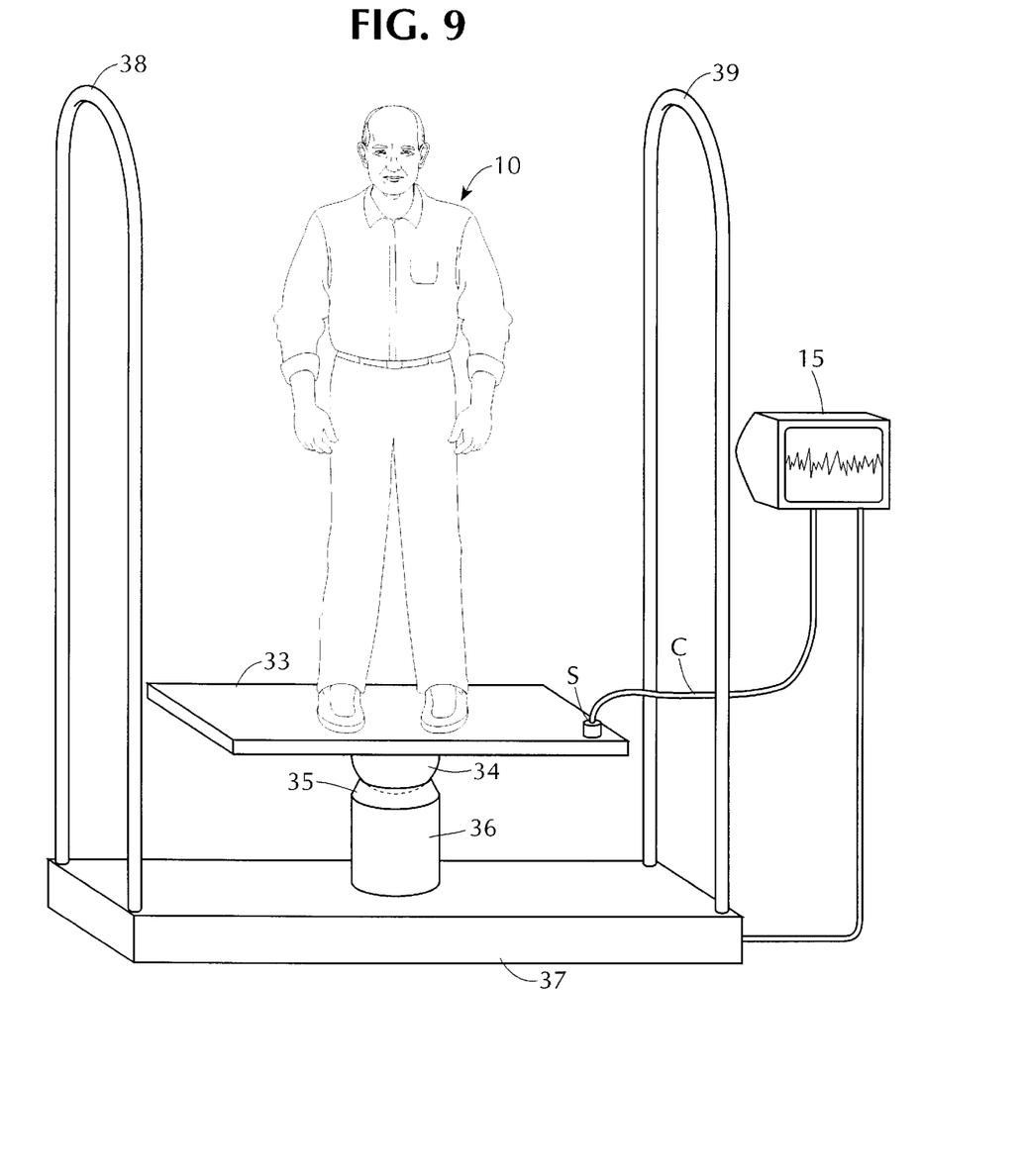
FIG. 9 shows a third embodiment of an unsteady platform in accordance with the invention.

In the arrangement shown in FIG. 9, an unsteady platform 33 on which patient 10 stands is provided with a sensor box S containing clinometers CA and CB. These are coupled via cable C to the computer whose output is applied to video monitor 15 as in the previous embodiments. Platform 33 is anchored on a hemispherical ball 34 rotatable within a socket 35 whose cavity matches the spherical surface of the ball as in a universal joint. Hence platform 33 may be tilted in any direction by patient 10 as he undergoes a stability test. Socket 35 is supported on top of a cylindrical post 37 anchored on a stable base 37 which rests on a horizontal ground surface.

Mounted at opposite ends of base 37 are a pair of hoop-shaped security rails 38 and 39 which patient 10 may grasp should he feel the need to steady himself.

The unsteady platform shown in FIG. 9 acts to test the stability of a patient in the same manner previously disclosed in connection with the other embodiments of an unsteady platform.

While there have been shown preferred embodiment of a dynamic system in accordance with the invention, it is to be understood that many changes may be made therein without departing from the spirit of the invention.

I claim:

1. A dynamic system adapted to test a human subject to determine the degree to which his physical stability is impaired without regard to the cause of impairment, the system comprising:

A. an unsteady platform on which the subject to be tested stands, the platform being supported at a raised position above ground to normally lie in a horizontal plane having an X axis which extends through the center of the platform and a Y axis which is normal to the X axis and extends through said center, said platform being rockable by said subject about said X and Y axes to thereby change the orientation of the platform;

B. electronic sensors mounted on said platform yielding electrical signals which depend on the deviation of the platform from the X and Y axes which when the subject standing on the platform shifts his weight thereon to change the orientation of the platform, whereby the resultant signals are indicative of the degree to which the stability of the subject is impaired; and C. means responsive to said signals to present on a screen viewable by the subject an image whose position on the screen is indicative of the changing orientation of the platform.

2. A system as set froth in claim 1, in which said electronic sensors are constituted by a pair of electronic clinometers, one being aligned with the X axis and the other with the Y axis.

3. A system as set forth in claim 1, in which the unsteady platform is formed by a convex dish that rests on a ground surface and has a flat top face raised above ground, said dish when a subject stands on said flat face, being rockable by the subject.

4. A system as set forth in claim 1, in which the unsteady platform is formed by a circular disc lying within a gimbal and hinged thereto to be rockable about said X-axis; said gimbal lying within a circular opening in a base plate raised above ground, and being hinged to said base plate to be rockable about said Y axis.

5. A system as set forth in claim 4, in which the base plate is mounted on legs of adjustable height.

6. A system as set forth in claim 4, in which side rails are attached to the base plate.

7. A system as set forth in claim 1, in which the unsteady platform is formed by a plate attached to a ball rotatable within a socket mounted on a post anchored on a horizontal base, whereby when a subject stands on said plate the plate is rockable by the subject about said X and Y axes.

8. A system as set forth in claim 1, further including a computer whose output is applied to a video monitor having a screen on which are presented a computer-generated cursor and a target which appears at a corner of the screen, the signals from the sensors being fed into the computer to control the position of the cursor whereby the subject standing on the platform and viewing the screen, by shifting his weight can cause the cursor to move toward and acquire the target.

9. A system as set forth in claim 8, in which the cursor has the form of a cross created by intersecting horizontal and vertical bars that fit within an imaginary square.

10. A system as set forth in claim 9, in which the target is formed by a square box which matches said imaginary square and is framed by a square border, the cursor acquiring said target when its point of intersection lies within the box.

11. A system as set forth in claim 10, in which the computer is provided with a tone generator which produces a tone of one frequency when the target is acquired by the cursor and a tone of another frequency when the point of intersection is outside the box of the target.

12. A system as set forth in claim 8, in which the computer includes means to measure the time it takes for the cursor to move from a center position on the screen to a position at which it acquires the target.

13. A system as set forth in claim 8, in which the computer includes means to measure the time it takes for the subject to react to the target when it is first presented on the screen to cause the cursor to move toward the target.

14. A system as set forth in claim 8, in which the computer includes means to measure the total distance travelled by the cursor once it acquires the target divided by a predetermined number of seconds.

* * * * *